United States Patent [19]

Brand

[11] Patent Number: 4,812,446

[45] Date of Patent: Mar. 14, 1989

[54] PHARMACEUTICAL PRODUCTS PROVIDING ENHANCED ANALGESIA

[75] Inventor: Larry M. Brand, West Chester, Ohio

[73] Assignee: The Procter & Gamble Company, Cincinnati, Ohio

[21] Appl. No.: 74,655

[22] Filed: Jul. 17, 1987

Related U.S. Application Data

[62] Division of Ser. No. 684,642, Dec. 24, 1984, Pat. No. 4,681,897.

[51] Int. Cl.$^4$ .................... A61K 31/60; A61K 31/13; A61K 31/16
[52] U.S. Cl. .................................. 514/165; 514/579; 514/627; 514/816
[58] Field of Search ............... 514/627, 629, 605, 165, 514/568, 579, 584

[56] References Cited

U.S. PATENT DOCUMENTS

| | | | |
|---|---|---|---|
| 3,060,091 | 10/1962 | Witkin | 514/282 |
| 3,106,513 | 10/1963 | Reinhard | 514/282 |
| 3,110,650 | 11/1963 | Fischer et al. | 514/282 |
| 4,083,981 | 4/1978 | Yamamoto et al. | 514/282 |
| 4,216,212 | 8/1980 | Flora et al. | 514/282 |
| 4,238,508 | 12/1980 | Nelson | 514/629 |
| 4,264,582 | 4/1981 | Flora et al. | 514/102 |
| 4,269,828 | 5/1981 | Flora et al. | 514/102 |
| 4,275,059 | 6/1981 | Flora et al. | 514/108 |
| 4,282,214 | 8/1981 | Flora et al. | 514/102 |
| 4,313,958 | 2/1982 | LaHann | 514/629 |
| 4,315,936 | 2/1982 | Capetola et al. | 514/282 |
| 4,379,789 | 4/1983 | Capetola et al. | 514/282 |
| 4,401,663 | 8/1983 | Buckwalter et al. | 514/605 |
| 4,404,210 | 9/1983 | Schmidt | 514/282 |
| 4,407,804 | 10/1983 | Schmidt | 514/282 |
| 4,407,805 | 10/1983 | Schmidt | 514/282 |
| 4,424,205 | 1/1984 | LaHann et al. | 514/72 |
| 4,443,473 | 5/1984 | Buckwalter et al. | 514/487 |
| 4,493,848 | 1/1985 | Buckwalter et al. | 514/629 |
| 4,532,139 | 7/1985 | Janusz et al. | 514/627 |
| 4,544,668 | 10/1985 | Janusz et al. | 514/563 |
| 4,544,669 | 10/1985 | LaHann et al. | 514/563 |

OTHER PUBLICATIONS

Arvier, P. T., L. A. Chahl and R. J. Ladd, "Modification by Capsaicin and Compound 48/80 of Dye Leakage Induced by Irritants in the Rat", *British Journal of Pharmacology*, vol. 59, pp. 61–68 (1977).

Yaksh, T. L., D. H. Farb, S. E. Leeman, T. M. Jessell, "Intrathecal Capsaicin Depletes Substance P in the Rat Spinal Cord and Produces Prolonged Thermal Analgesia", *Science*, vol. 206, pp. 481–483 (1979).

Virus, R. M. and G. F. Gebhart, "Pharmacologic Actions of Capsaicin: Apparent Involvement of Substance P in Serotonin", *Life Sciences*, vol. 25, pp. 1273–1284 (1979).

Verbeeck, R. K., J. L. Blackburn and G. R. Loewen, "Clinical Pharmokinetics of Non-Steroidal Anti-Inflammatory Drugs" *Clinical Pharmokinetics*, vol. 8, pp. 297–331 (1983).

Kiernan, J. A., "A Study of Chemically Induced Acute Inflammation in the Skin of the Rat", *Quarterly Journal of Experimental Physiology*, vol. 62, pp. 151–161 (1977).

Jancso, N., A. Jancso-Jabor and J. Szolcsanyi, "Direct Evidence for Neurogenic Inflammation and its Prevention by Denervation and by Pretreatment by Capsaicin", *British Journal of Pharmaceutical Chemotherapy*, vol. 31, pp. 138–151 (1967).

*Primary Examiner*—John W. Rollins
*Attorney, Agent, or Firm*—Milton B. Graff, IV; Jack D. Schaeffer; Richard C. Witte

[57] ABSTRACT

An analgesic composition comprising capsaicin or a capsaicin analogue and an analgesic selected from the class of non-steroidal anti-inflammatory, antipyretic and analgesic drugs is disclosed. This combination has been found to exhibit unexpectedly enhanced analgesic activity in humans and lower animals without a corresponding increase in undesirable side effects.

17 Claims, No Drawings

PHARMACEUTICAL PRODUCTS PROVIDING ENHANCED ANALGESIA

This is a division of application Ser. No. 684,642, filed on Dec. 24, 1984, now U.S. Pat. No. 4,681,897.

TECHNICAL FIELD

The present invention relates to analgesic compositions comprising capsaicin or a capsaicin analog combined with a drug selected from the class of non-steroidal anti-imflammatory, antipyretic and analgesic compounds. These compositions, when administered to humans or lower animals, provide a synergistic analgesic effect while minimizing undesirable side effects and toxicity.

Capsaicin and its derivatives appear to produce an analgesic effect through a mechanism largely unrelated to that of the other two categories of analgesics, opioids (narcotics) and non-steroidal analgesics (aspirin-like drugs). Since both capsaicin and the non-steroidals produce an analgesic effect, although apparently through different mechanisms, it might be expected that their combined effect would be at best additive. However, tests have shown that the analgesic effect of the combination is not merely the sum of the effects of each component, but rather an unexpected, greatly enhanced synergistic effect. Furthermore, the undesirable side effects of the two categories of analgesics are not closely related and the addition of the second analgesic does not appear to potentiate the side effects of the first. It is therefore possible to combine the two analgesics in such a dosage as to provide greatly enhanced analgesia with no enhancement of side effects. Depending on the dosages employed, the capsaicin may either potentiate the degree of analgesia beyond that obtainable using the non-steroidal alone, or it may induce analgesia at dosages where no analgesic effect is obtained from either component alone.

BACKGROUND OF THE INVENTION

Traditionally, analgesics have fallen into two broad categories. Simple, non-narcotic analgesics, such as aspirin, which appear to work by inhibition of prostaglandin synthetase, are effective against pain of integumental origin such as headache and muscle aches, but are often ineffective in controlling deeper, more intense pain. Furthermore, they may cause undesirable side effects even at therapeutic dosages. The most common of these side effects is a propensity to induce dyspepsia and gastrointestinal bleeding. At higher dosages, the salicylates may have toxic effects on the central nervous system consisting of stimulation (including convulsions) followed by depression. Headache, dizziness, mental confusion, hearing difficulties and hyperventilation may also occur. Gastrointestinal symptoms may include epigastric distress, nausea and vomiting. The narcotic analgesics appear to work through interaction with the endorphin/enkephalin receptor system of the central nervous system and are useful in controlling pain which is too intense to be controlled by the weaker, non-narcotic analgesics. However, centrally-acting narcotic analgesics have several serious undesirable side effects, including the development of physical dependence and tolerance, sedation, respiratory depression, hypotension, increase in cerebrospinal fluid pressure, nausea, vomiting and constipation. In some patients, particularly the chronically ill, the narcotic side effects make it impossible to administer dosages sufficient to adequately control pain over the required time period.

This invention combines capsaicin or a capsaicin analog with a drug from the class of non-narcotic, non-steroidal anti-inflammatory, antipyretic and analgesic compounds (often referred to as "aspirin-like" drug, since the prototypical compound is aspirin), producing a synergistic increse in analgesia without a corresponding increase in side effects. The degree of analgesia produced by this combination has been found in some cases to be equivalent to that formerly obtainable only through the use of narcotics. Thus, the claimed combination makes it possible to control pain which is too severe to be adequately controlled by the non-steroidals alone, while avoiding the serious side effects and addiction potential inherent in the use of opioids.

It has been recently discovered that capsaicin, a natural product of certain species of the genus *Capsicium*, induces analgesia. Capsaicin (8-methyl-N-vanillyl-6Z-nonenamide) and "synthetic" capsaicin (N-vanillylnonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al, *Science*, 206, pp 481–483 (1979); Jancso, et al, *Naunyn-Schmiedeberg's Arch. Pharmacol.*, Vol. 311, pp 285–288 and Holzer et al, *Eur. J. Pharm.* Vol. 58, pp 511–514 (1979). U.S. Pat. No. 4,238,505, Nelson, issued Dec. 9, 1980, discloses 3-hydroxyacetanilide for use in producing analgesia in animals. European Patent Application No. 0089710, LaHann, et al, published Sept. 28, 1983, describes hydroxyphenylacetamides with analgesic and anti-irritant activity. Similarly, analgesic and anti-irritant activity is disclosed for N-vanillylsulfonamides in U.S. Pat. No. 4,401,663, Buckwalter, et al, issued Aug. 30, 1983; N-vanillylureas in European Patent Application No. 0068590, Buckwalter, et al, published Jan. 5, 1983; N-vanillylcarbamates in European Patent Application No. 0068592, Buckwalter, et al, published Jan. 5, 1983; N-[(substituted phenyl)methyl]alkynlamides in U.S. patent application Ser. No. 514,204, Janusz, et al, filed July 14, 1983; methylene substituted N-[(substituted phenyl)methyl]-alkanamides in U.S. patent application Ser. No. 514,205, Janusz, et al, filed July 14, 1983; N[(substituted phenyl)methyl]-cis-monounsaturated alkenamides in U.S. patent application Ser. No. 514,206, LaHann, et al, filed July 14, 1983; and N-[substituted phenyl)methyl]-diunsaturated amides in U.S. patent application Ser. No. 514,207, LaHann, et al, filed July 14, 1983. However, none of these references suggest in any way the desirability of concurrent administration of capsaicin or a capsaicin derivative with a non-steroidal. Further, the art suggests that it is extremely difficult to predict when a synergistic effect will be obtained from the concurrent administration of two pharmaceutical compounds which take effect through different mechanisms.

Although there are many patents which disclose analgesic and anti-inflammatory compositions containing a combination of two or more mechanistically unrelated analgesic and/or anti-inflammatory compounds, none of these compounds has a structure at all similar to that of capsaicin. See U.S. Pat. No. 4,404,210, Schmidt, issued Sept. 13, 1983; U.S. Pat. No. 4,083,981, Yamamoto, issued Apr. 11, 1978; U.S. Pat. No. 4,315,936, Capetola et al, issued Feb. 16, 1982; U.S. Pat. No. 4,379,789, Capetola et al, issued Apr. 12, 1983; and U.S. Pat. No. 4,275,059, Flora, et al, issued June 23, 1981.

Thus, based on the art, one could not have predicted that the combination of capsaicin or a capsaicin analog with a non-steroidal would result in a synergistic increase in analgesia.

SUMMARY OF THE INVENTION

It has now been found that combinations of capsaicin derivatives of the general formula

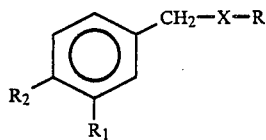

wherein $R_1$ is OH or $OCH_3$, $R_2$ is OH or a short-chain ester, X is

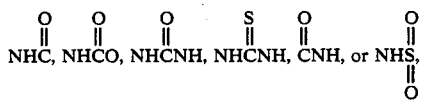

and R is a $C_5-C_{11}$ alkyl, $C_5-C_{11}$ alkenyl, $C_{11}-C_{23}$ cis alkenyl, $C_{11}-C_{23}$ alkynyl, $C_{11}-C_{23}$ alkadienyl, or $C_{11}-C_{23}$ methylene substituted alkane, with a non-steroidal analgesic at weight ratios of capsaicinoid to non-steroidal from about 20:1 to 1:20, and preferably from about 10:1 to 1:10, provide unexpectedly enhanced analgesic activity in humans and lower animals without a corresponding increase in undesirable side effects.

Another aspect of the present invention comprises the method of alleviating pain in humans and lower animals by concurrent administration of a safe and effective amount of the analgesic composition described above.

DETAILED DESCRIPTION OF THE INVENTION

Definitions

By the term "comprising" as used herein is meant that various other inert ingredients, compatible drugs and medicaments, and steps can be employed in the compositions and methods of the present invention as long as the critical capsaicinoid/non-steroidal combination is present in the compositions and is used in the manner disclosed. The term "comprising" thus encompasses and includes the more restrictive terms "consisting essentially of" and "consisting of" which characterize the use of the compositions and methods disclosed herein.

By "compatible" herein is meant that the components of the composition are capable of being commingled without interacting in a manner which would substantially decrease the analgesic efficacy of the total composition under ordinary use situations.

By "administer concurrently" is meant either the administration of a single composition containing both the capsaicinoid and the non-steroidal, or the administration of the capsaicinoid and the non-steroidal as separate compositions within a short enough time period that the effective result is equivalent to that obtained when both compounds are administered as a single composition. Normally this would involve two separate dosages given within 10 minutes of each other. However, since many capsaicinoids retain effectiveness over unusually long time periods (possibly up to 3 days in the same cases) and most non-steroidals provide effective analgesia for relatively short time periods (4–8 hours), it may be desirable in some cases to implement a therapeutic regimen whereby each component is administered according to a schedule determined by its own period of analgesic effectiveness in order to maintain optimum effectiveness of the combination. The preferred method of administration is as a single composition.

All percentages and ratios herein are by weight unless otherwise specified.

Compositions

The compositions of the present invention comprise a safe and effective amount of:

(a) capsaicin or a capsaicin analog, (b) a compound selected from the group of non-steroidal anti-inflammatory, antipyretic and analgesic drugs, and their pharmaceutically-acceptable salts; and (c) a pharmaceutically-acceptable carrier.

A safe and effective amount of the composition is that amount which provides analgesia, thereby alleviating or preventing the pain being treated at a reasonable benefit/risk ratio, as is intended with any medical treatment. Obviously, the amount of the composition used will vary with such factors as the particular condition that is being treated, the severity of the condition, the duration of the treatment, the physical condition of the patient, the nature of concurrent therapy (if any), the method of administration, and the specific formulation and carrier employed.

By the term "capsaicin or a capsaicin analog" or "capsaicinoid" is meant a compound of the general formula

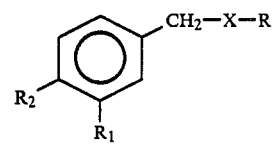

wherein $R_1$ is selected from the group consisting of OH and $OCH_3$, $R_2$ is selected from the group consisting of

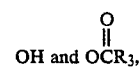

$R_3$ is selected from the group consisting of a $C_1-C_4$ alkyl, phenyl, and methyl, X is selected from the group consisting of

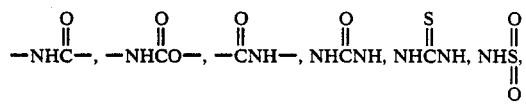

and R is selected from the group consisting of a $C_5-C_{11}$ alkyl, $C_5-C_{11}$ alkenyl, $C_{11}-C_{23}$ cis alkenyl, $C_{11}-C_{23}$ alkynyl, $C_{11}-C_{23}$ alkadienyl and $C_{11}-C_{23}$ methylene substituted alkane.

Preferred compounds include those wherein both $R_1$ and $R_2$ are OH and X is

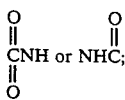

and those wherein $R_1$ is $OCH_3$, $R_2$ is OH or $R_3CO$ and X is

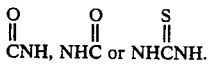

Preferred R groups include $C_7$–$C_{10}$ alkyls and trans alkenyls, and $C_{16}$–$C_{21}$ cis alkenyls and alkadienyls. The preferred moieties within these groups include $C_8H_{17}$, $C_9H_{17}$ and $C_{17}H_{33}$. Preferred capsaicin analogs include N-vanillyl-alkadienamides, N-vanillyl-alkanedienyls, and N-vanillyl-cis-monounsaturated alkenamides. A particularly preferred capsaicinoid is N-vanillyl-9Z-octadecenamide (N-vanillyloleamide).

Preferred capsaicin analogs and methods for their preparation are described in the following Patents and Patent Applications, all incorporated by reference herein: Capsaicin (8-methyl-N-vanillyl-6E-nonenamide) and "synthetic" capsaicin (n-vanillylnonanamide) are disclosed as analgesics in U.S. Pat. No. 4,313,958, La-Hann, issued Feb. 2, 1982. European Patent Application No. 0089710, LaHann, et al, published Sept. 28, 1983, describes hydroxyphenylacetamides with analgesic and anti-irritant activity. Similary, analgesic and anti-irritant activity is disclosed for N-vanillylsulfonamides in European Patent Application No. 0068591, Buckwalter, et al, published Jan. 5, 1983; N-vanillylureas in European Patent Application No. 0068590, Buckwalter, et al, published Jan. 5, 1983; N-vanillylcarbamates in European Patent Application No. 0068592, Buckwalter, et al, published Jan. 5, 1983; N-[(substituted phenyl)methyl]alkynylamides in U.S. patent application Ser. No. 514,204, Janusz, et al, filed July 14, 1983; methylene substituted-N-[(substituted phenyl)methyl]-alkanamides in U.S. patent application Ser. No. 514,205, Janusz, et al, filed July 14, 1983; N[(substituted phenyl)methyl]-cis-monounsaturated alkenamides in U.S. patent application Ser. No. 514,206, LaHann, et al, filed July 14, 1983; and N-[(substituted phenyl)methyl]-diunsaturated amides in U.S. patent application Ser. No. 514,207, La-Hann, et al, filed July 14, 1983.

By "non-steroidal anti-inflammatory, antipyretic and analgesic drugs", or "non-steroidal", is meant a heterogeneous group of compounds, often chemically unrelated (although most of them are organic acids) which share certain therapeutic actions and side effects. Their therapeutic activity appears to depend to a large extent upon the inhibition of prostaglandin biosynthesis. Their primary use is to provide symptomatic relief from pain and inflammation associated with certain diseases, particularly musculoskeletal disorders such as rheumatoid arthritis and osteoarthritis. These compounds are often referred to as "aspirin-like drugs", since the prototypical compound is aspirin. The pharmacological properties and therapeutic uses of the compounds included within this classification are described in detail in Goodman and Gilman, "Analgesic-Antipyretics and Antiinflammatory Agents; Drugs Employed in the Treatment of Gout", *The Pharmacological Basis of Therapeutics*, 6th Ed., Ch. 29 (1980); Verbeeck et al, "Clinical Pharmacokinetics of Non-steroidal Anti-inflammatory Drugs", *Clinical Pharmakinetics* 8, pp 297–331 (1983), and Scherrer and Whitehouse, *Antiinflammatory Agents Chemistry & Pharmacology*, Vol. 1, Academic Press, New York (1974); all incorporated by reference herein.

Specific classes of non-steroidals useful in the present invention are disclosed in detail in the following U.S. Patents, all incorporated by reference herein: U.S. Pat. No. 4,275,059, Flora, et al, issued June 23, 1983, discloses salicylic acid, its pharmaceutically-acceptable salts, and its pharmaceutically-acceptable esters and derivatives; U.S. Pat. No. 4,264,582, Flora, et al, issued Apr. 28, 1981, discloses p-(isobutylphenyl) acetic acid compounds, including the parent acid (ibufenac) and its salts and esters, and derivatives thereof; U.S. Pat. No. 4,282,214, Flora, et al, issued Aug. 4, 1981, discloses various phenylacetic acid derivatives, their pharmaceutically-acceptable salts, and their pharmaceutically-acceptable esters; U.S. Pat. No. 4,216,212, Flora, et al, issued Aug. 5, 1980, discloses pyrazolidine compounds, their pharmaceutically-acceptable salts, and their pharmaceutically-acceptable esters; U.S. Pat. No. 4,269,828, Flora, et al, issued May 26, 1981, discloses indole compounds, their pharmaceutically-acceptable salts, and their pharmaceutically-acceptable esters.

Specifically preferred non-steroidals may be roughly divided into four general classifications. The salicylates include compounds such as acetylsalicylic acid (aspirin), salicylic acid, sodium salicylate, diflunisal, and methyl salicylate. The salicylate-like anti-inflammatory agents include compounds such as phenylbutazone, indomethacin, zomapirac acid, sulindac, fluproquazone, and mefenamic acid. The arylalkanoic acids include ibuprofen, naproxen, ketoprofen, fenoprofen, suprofen, flurbiprofen, benoxaprofen, pirprofen, and carprofen. The salicylate-like analgesic-antipyretics include acetaminophen and phenacetin. In some cases, the non-steroidals may be mixed with each other or with other drugs such as caffeine. Two popular analgesic combinations are aspirin, phenacetin and caffeine (APC) and aspirin, phenacetin and acetaminophen. Non-steroidals most preferred for use in the capsaicinoid-non-steroidal combination include acetylsalicylic acid (aspirin), ibuprofen, acetaminophen, diflunisal, naproxen, fenoprofen, and mefenamic acid. A specifically preferred combination is APC.

Weight ratios of capsaicinoid to non-steroidal useful in the present invention range from about 20:1 to about 1:20, with the preferred ratio ranging from about 10:1 to about 1:10. The optimum weight ratio is dependent primarily upon the relative strength of the particular capsaicinoid and non-steroidal used, and the type of severity of the pain being treated. As a representative example, preferred weight ratios of capsaicinoid:acetylsalicylic acid (aspirin) may range from about 3:1 to about 1:3; preferred weight ratios of capsaicinoid:diflunisal may range from about 3:1 to about 1:3; preferred weight ratios of capsaicinoid:acetaminophen may range from about 3:1 to about 1:3; and preferred weight ratios of capsaicinoid:ibuprofen may range from about 5:1 to about 1:5. The preferred weight ratio for the preferred combination of N-vanillyl-9Z-octadecenmaide and aspirin is about 2:1.

By "pharmaceutically acceptable salts" is meant those salts of the above disclosed acids which are toxicologically safe for topical or oral administration. These include the sodium, calcium, potassium, magnesium, ammonium, lysine, and arginine salts.

By "pharmaceutically acceptable carrier" is meant a solid or liquid filler, diluent or encapsultaing substance which may be safely used in systemic or topical administration. Depending upon the particular route of administration, a variety of pharmaceutically-acceptable carriers, well-known in the art, may be used. These include solid or liquid fillers, diluents, hydrotropes, surface-active agents, and encapsulating substances. The amount of the carrier employed in conjunction with the capsaicinoid/opioid combination is sufficient to provide a practical quantity of material per unit dose of analgesic.

Pharmaceutically-acceptable carriers for systemic administration, that may be incorporated into the compositions of this invention, include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Specific pharmaceutically-acceptable carriers are described in the following U.S. patent applications, all incorporated by reference herein: U.S. Pat. No. 4,401,663, Buckwalter, et al, issued Aug. 30, 1983; European Patent Application No. 089710, LaHann, et al, published Sept. 28, 1983; and European Patent Application No. 0068592, Buckwalter, et al, published Jan. 5, 1983. Preferred carriers for parenteral administration include propylene glycol, ethyl oleate, pyrrolidone, aqueous ethanol, sesame oil, corn oil, and combinations thereof.

Various oral dosage forms can be used, including such solid forms as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents. Preferred carriers for oral administration include ethyl oleate, methyl cellulose, gelatin, propylene glycol, cottonseed oil, sesame oil, peanut oil, corn oil, soybean oil, oil and water emulsions, and self-emulsifying oils either as free-flowing liquids or encapsulated in soft gelatin capsules. Specific examples of pharmaceutically-acceptable carriers and excipients that may be used to formulate oral dosage forms, which may be used in formulating oral dosage forms containing monoalkenamides, are described in U.S. Pat. No. 3,903,297. Robert, issued Sept. 2, 1975, incorporated by reference herein. Techniques and compositions for making solid oral dosage forms are described in Marshall, "Solid Oral Dosage Forms", *Modern Pharmaceutics*, Vol. 7, (Banker and Rhodes, editors), 359–427 (1979), incorporated by reference herein.

Specific systemic and topical formulations useful in this invention are described in the following U.S. patent applications, relating to specific capsaicin analogs and methods of treatment, which are incorporated by reference herein: U.S. Pat. No. 4,401,663, Buckwalter, et al, issued Aug. 30, 1983; and European Patent Application No. 0089710; LaHann, et al, published Sept. 28, 1983; European Patent Application No. 0068590, Buckwalter, et al, published Jan. 5, 1983; and European Patent Application No. 0068592, Buckwalter, et al, published Jan. 5, 1983. Topical vehicles, useful herein, are disclosed in the following U.S. patent applications, incorporated by reference herein: "Improved Penetrating Topical Pharmaceutical Compositions Combining 1-dodecylazacycloheptan-2-one", Ser. No. 506,275, Cooper, filed June 21, 1983; "Penetrating Topical Pharmaceutical Compositions Containing N-(1-hydroxyethyl)-pyrrolidone", Ser. No. 506,273, Cooper, filed June 21, 1983; and "Compounds Useful for Producing Analgesia", Ser. No. 514,206, LaHann and Buckwalter, filed July 14, 1983.

Methods for Producing Analgesia

The present invention also encompasses methods for providing analgesia in humans or lower animals by administering concurrently to the human or lower animal in need of such treatment a safe and effective amount of a capsaicinoid/non-steroidal combination or a composition containing the same. Dosages required, as well as methods of administration, are dependent on the type of nonsteroidal employed, the physical condition of the patient, the severity of the pain which must be prevented or alleviated, the relative severity and importance of adverse side effects, and other factors within the judgment of the physician. The preferred method of administration in most cases will be orally.

The maximum dosage of the preferred capsaicin analogue vanillyloleamide (VO) which would normally be administered orally to an average adult without unacceptable side effects is about 2000 mg (35.4 mg/kg). The minimum effective dosage is about 50 mg (0.85 mg/kg). The maximum dosage of a non-steroidal which can be administered to the average adult is also about 2000 mg (35.4 mg/kg). Thus, the maximum allowable dosage of the combination will be about 2000 mg (35.4 mg/kg). It should be noted that a sub-effective dosage of one compound may effectively potentiate the other compound; therefore, less-than-minimum dosages of each component may be utilized in some cases. Thus, when dealing with safe and effective dosage levels of the present invention, it is more appropriate to speak of safe and effective dosages of the combination rather than of the individual components.

The compositions and combinations of this invention can be used to treat and prevent pain and inflammation associated with certain diseases, particularly muscularskeletal disorders, and to provide analgesia in various disorders at the deeper structures, muscles, tendons, bursa and joints associated with disease and trauma, and in various other conditions in which capsaicinoids and/or non-steroidals have heretofore been used to alleviate pain and discomfort.

The compositions of the instant invention are normally administered either topically or orally.

The following non-limiting Examples illustrate the compositions, methods of treatment, and uses of the present invention.

EXAMPLE I

An analgesic composition for oral administration was made using the following ingredients:
N-Vanillyl-9Z-octadecenamide: 120 mg
Aspirin: 60 mg
Methylcellulose: 30 mg
Saline: 6.0 ml The composition was prepared by dissolving the methylcellulose in the saline to yield a 0.5% solution, after which the solid aspirin and N-vanillyl-9-octadecenamide were added and uniformly suspended in the solution by exposure to sonication. Male mice weighing approximately 25 g were orally dosed with a volume of this suspension sufficient to deliver 200 mg/kg of the octadecenamide and 100 mg/kg of the aspirin. Identical groups of mice were dosed orally with similarly prepared formulations which lacked either the aspirin, the octadecenamide, or both. Analgesic activity was demonstrated using the phenylquinone writhing test.

EXAMPLE II

An analgesic composition for oral administration was made using the following ingredients:
N-vanillyl-9Z-octadecenamide: 120 mg
Ibuprofen: 30 mg
Methylcellulose: 30 mg
Saline: 6.0 ml The methylcellulose suspending agent was dissolved in the saline to yield a 0.5% solution, to which the two drugs were added. A homogeneous suspension was achieved by the aid of sonication. Male mice weighing approximately 25 g were dosed by gavage with 250 mg/kg of the mixture. Analgesic activity was demonstrated using the phenylquinone writhing test.

EXAMPLE III

An analgesic composition for oral administration was made using the following ingredients:
N-vanillyl-9Z-octadecenamide: 120 mg
Iburofen: 30 mg
Ethyl oleate: 6.0 ml The two analgesic agents were suspended in the ethyl oleate with the aid of sonication, and analgesic activity was demonstrated using the phenylquinone writhing test.

EXAMPLE IV

An analgesic composition for oral administration is made using the following ingredients:
N-vanillyl-9Z-octadecenamide: 100 g
Acetylsalicylic acid: 100 g
Ethyl oleate: 300 g The composition is made by simple dissolution of the octadecenamide in the ethyl oleate, followed by suspension of the finely divided acetylsalicylic acid in the resulting solution by vigorous mechanical blending under an inert atmosphere of argon or dry nitrogen. The creamy suspension is then loaded into soft gelatin capsules to deliver 325 mg acetylsalicylic acid and 325 mg N-vanillyl-9-octadecenamide per capsule. One such capsule is administered orally to a 60 kg human, producing analgesia.

Substantially similar results are produced when the octadecenamide is replaced, in whole or in part by capsaicin; N-vanillyl-9E-octadecenamide; N-[(4-acetoxy-3-methoxyphenyl)methyl]-9Z-octadecenamide; N-vanillyl-(Z,Z)-9,12-octadecadienamide; N-vanillyl-(E,E)-9,12-octadecadienamide; N-[(4-acetoxy-3-methoxyphenyl)methyl]-(E,E)-9,12-octadecadienamide; N-vanillyl-(E,E)-10,13-nonadecadienamide; N-vanillyl-9-octadecynamide; 9-methylene-N-octadecanamide; 9-methylene-N-[(4-acetoxy-3-methoryphenyl)methyl]octadecanamide; 4-acetoxy-3-methoxy-benzyl nonamide, or octyl 3,4-dehydroxyphenylacetamide.

Substantially similar results are also obtained when the acetylsalicylic acid is replaced, in whole or in part, by the sodium, calcium, or lysine salts of aspirin, ibuprofen, diflunisal, naproxen, mefenamic acid, fenoprofen, indomethacin, ketoprofen, suprofen, perprofen, carprofen, or an aspirin-phenacetin-caffeine combination (APC).

EXAMPLE V

A composition for oral administration is made with the following components:

| | Bulk | Individual Tablet |
|---|---|---|
| N—vanillyl-9,12-octadecadienamide | 140 g | 350 mg |
| Ibuprofen | 35 g | 90 mg |
| Starch | 12 g | 30 mg |
| Magnesium stearate | 2 g | 5 mg |
| Microcrystalline cellulose | 40 g | 100 mg |
| Colloidal silicon dioxide | 1 g | 2.5 mg |
| Povidone | 5 g | 12.5 mg |

The above ingredients are admixed in bulk and formed into compressed tablets, using tabletting methods known in the art, each containing 590 mg of the mixture. One such tablet is administered orally to a 60 kg human, producing analgesia.

EXAMPLE VI

A composition for oral administration is made with the following ingredients:
N-vanillyl-9Z-octadecenamide: 225 g
Aspirin: 125 g
Phenacetin: 83 g
Caffeine: 17 g
Mannitol: 487 g
Acacia: 29.3 g
Starch: 48.1 g
Talc: 15 g
Calcium stearate: 2 g The above ingredients are admixed in bulk and formed into tablets weighing 100 mg each using tabletting methods known in the art. Two such tablets are administered orally to a 70 kg human, producing analgesia.

EXAMPLE VII

A composition for transdermal topical delivery is made by admixing the following components:
N-vanillyl-9,12,15[E,E,E]-octadecatrienamide: 4.0%
Ibuprofen: 1.0%
Myristyl alcohol: 1.0%
Propylene glycol: 94.0%

Approximately 4.0 ml of the lotion is applied to an 80 sq. cm. portion of the skin of a 60 kg human, producing analgesia.

Effectiveness in Providing Analgesia Phenylquinone Writhing Tests

The extent of analgesia obtained was determined using the phenylquinone writhing test model. Groups of eight male mice weighing between approximately 25 and 30 g were dosed orally by gavage with the analgesic composition to be tested. Identical groups of mixe were dosed with control compositions. Three hours after this initial administration, the mice were injected intraperitoneally with a 0.2% solution of phenylbenzoquinone in aqueous ethanol. The ability of the analgesic compositions tested to relieve the discomfort induced was measured by counting the number of abdominal contractions, or "writhes", occurring in each mouse during a 10 minute period beginning 10 minutes after injection of the phenylbenzoquinone solution. The results are expressed as a percent of the "writhing" response observed in the vehicle control group.

EXAMPLE VIII

An analgesic composition for oral administration was made using the following ingredients:
N-vanillyl-9-octadecenamide: 120 mg
Aspirin: 60 mg
Methylcellulose: 30 mg
Saline: 6.0 ml The composition was prepared by dissolving the methylcellulose in the saline to yield a 0.5% solution, after which the solid aspirin and N-vanillyl-9-octadecenamide were added and uniformly suspended in the solution by exposure to sonication.

Male mice weighing approximately 25 g were orally dosed with a volume of this suspension sufficient to deliver 200 mg/kg of the octadecenamide and 100 mg/kg of the aspirin. Identical groups of mice were dosed orally with similarly prepared formulations which lacked either the aspirin, the octadecenamide, or both. The mouse "writhing" method for assessing pain response described above was used. The data, summarized in the following table, were normalized based on the vehicle control taken as 100.

| Treatment | % Writhing Response |
| --- | --- |
| Methylcellulose alone | 100 |
| Octadecenamide (200 mg/kg) | 54 |
| Aspirin (100 mg/kg) | 78 |
| Aspirin (100 mg/kg) + octadecenamide (200 mg/kg) | 10 |

The response of the group given aspirin alone was not statistically distinguishable from that of the control group. The 90% inhibition of the writhing response resulting from the combination treatment (aspirin plus octadecenamide) is greater than that expected from the sum of the aspirin treatment (22% inhibition) and octadecenamide treatment (45% inhibition) when given separately.

EXAMPLE IX

An analgesic combination for oral administration was prepared in a manner similar to that decribed for Example I, the only difference being the ratio of aspirin to N-vanillyl-9-octadecenamide:
N-vanillyl-9-octadecenamide: 120 mg
Aspirin: 120 mg
Methylcellulose: 30 mg
Saline: 6.0 ml A solution was prepared as described in Example I. The analgesic activity of the combination was assessed in mice using the "writhing" method described above. The activity of the combination was contrasted with those of similar formulations lacking the aspiring component, the octadecenamide component or both:

| Treatment | % Writhing Response |
| --- | --- |
| Methylcellulose alone | 100 |
| Aspirin (200 mg/kg) | 15 |
| Octadecenamide (200 mg/kg) | 33 |
| Aspirin (200 mg/kg) + octadecenamide (200 mg/kg) | 1.5 |

The analgesic efficacy obtained from the combination is significantly greater than that from either component alone.

EXAMPLE X

An analgesic composition for oral administration was made using the following ingredients:
N-vanillyl-9-octadecenamide: 120 mg
Ibuprofen: 30 mg
Methylcellulose: 30 mg
Saline: 6.0 ml The methylcellulose suspending agent was dissolved in the saline to yield a 0.5% solution, to which the two drugs were added. A homogeneous suspension was achieved by the aid of sonication. The analgesic efficacy of this formulation was evaluated by dosing the mice by gavage with a sufficient dosage to provide 250 mg/kg of the mixture. The analgesic strength of the treatment was assessed using the "writhing" method described above. The efficacy of the combination was compared with that of similar formulations lacking the octadecenamide, the ibuprofen, or both.

| Treatment | % Writhing Response |
| --- | --- |
| Methylcellulose alone | 100 |
| Ibuprofen (50 mg/kg) | 114 |
| Octadecenamide (200 mg/kg) | 48 |
| Octadecenamide (200 mg/kg) + ibuprofen (50 mg/kg) | 2 |

In this case, the addition of an ineffective dose of ibuprofen to a moderately effective dose of octadecenamide resulted in a greatly potentiated analgesic effect.

EXAMPLE XI

An analgesic composition for oral administration was made using the following ingredients:
N-vanillyl-9-octadecenamide: 120 mg
Ibuprofen: 30 mg
Ethyl oleate: 6.0 ml The two analgesics were suspended in ethyl oleate with the aid of sonication, and evaluated for analgesic efficacy exactly as described in Example X.

| Treatment | % Writhing Response |
| --- | --- |
| Ethyl oleate alone | 100 |
| Octadecenamide (200 mg/kg) | 36 |
| Ibuprofen (50 mg/kg) | 154 |
| Octadecenamide (200 mg/kg) + ibuprofen (50 mg/kg) | 5 |

Although the response of the group receiving 50 mg/kg of ibuprofen alone did not vary significantly from that of the control group, the addition of this sub-effective amount of ibuprofen to the octadecenamide greatly potentiated its analgesic effect. Further, the combination of ibuprofen with the octadecenamide can provide anti-inflammatory/anti-arthritis efficacy lacking in N-vanillyl-9-octadecenamide and related capsaicin analogs.

EXAMPLE XII

An analgesic composition for oral administration was made using the following ingredients:
N-vanillyl-9Z-octadecenamide: 120 mg
3-(2',4'-diflurophenyl)-salicylic acid: (diflunisal): 60 mg
Ethyl oleate: 6.0 ml The two analgesics were suspended in ethyl oleate with the aid of sonication and were evaluated for analgesic efficacy as described in Example X.

| TREATMENT | % WRITHING RESPONSE |
|---|---|
| Ethyl oleate alone | 100 |
| Diflunisal (100 mg/kg) | 121 |
| Octadecenamide (200 mg/kg) | 50 |
| Diflunisal (100 mg/kg) + Octadecenamide (200 mg/kg) | 15 |

In this case, the addition of an ineffective dose of diflunisal to a moderately effective dose of octadecenamide resulted in a greatly potentiated analgesic effect. Additionally, diflunisal provides anti-inflammatory activity not possessed by the octadecenamide alone.

EXAMPLE XIII

An analgesic composition for oral administration was made using the following ingredients:
N-vanillyl-9Z-octadecenamide: 75 mg
Acetaminophen: 75 mg
Ethyl oleate/benzyl alcohol (98:2 vol/vol): 5 ml The two analgesics were suspended in the ethyl oleate solution with the aid of sonication and were evaluated as in Example X.

| TREATMENT | % WRITHING RESPONSE |
|---|---|
| Ethyl oleate solution alone | 100 |
| Acetaminophen (150 mg/kg) | 127 |
| Octadecenamide (150 mg/kg) | 57 |
| Acetaminaphen (150 mg/kg) + octadecenamide (150 mg/kg) | 17 |

In this case, the addition of an ineffective dose of acetaminophen to a marginally effective dose of octadecenamide resulted in a greatly potentiated analgesic effect.

EXAMPLE XIV

In order to determine the preferred capsaicinoid:non-steroidal ratios, an analgesic combination for oral administration was made using the following ingredients:

1:1 Octadecenamide:aspirin Combination
N-vanillyl-9Z-octadecenamide: 75 mg
Aspirin: 75 mg
Ethyl oleate: 10 ml 1:2 Octadecenamide:aspirin Combination
N-vanillyl-9Z-octadecenamide: 50 mg
Aspirin: 100 mg
Ethyl oleate: 10 ml 1:5 Octadecenamide:aspirin Combination
N-vanillyl-9Z-octadecenamide: 25 mg
Aspirin: 125 mg
Ethyl oleate: 10 ml The two analgesics were suspended in ethyl oleate with the aid of sonication and were evaluated for analgesic efficacy as described in Example X.

| TREATMENT | % WRITHING RESPONSE |
|---|---|
| Ethyl oleate alone | 100 |
| 150 mg/kg aspirin | 92 |
| 150 mg/kg Octadecenamide | 43 |
| 150 mg/kg Octadecenamide:Aspirin (1:1) | 48 |
| 150 mg/kg Octadecenamide:Aspirin (1:2) | 28 |
| 150 mg/kg Octadeceaamide:Aspirin (1:5) | 77 |

The responses of the ethyl oleate control group, the 1:5 combination group (25 mg/kg octadecenamide + 125 mg/kg aspirin) and the group receiving 150 mg/kg aspirin were not significantly different. The groups receiving the octadecenamide alone and the 1:1 combination (75 mg/kg aspirin + 75 mg/kg octadecenamide) displayed a moderate analgesic effect. The group receiving the 1:2 combination (50 mg/kg octadecenamide + 100 mg/kg aspirin) displayed an analgesic effect unexpectedly superior to that of any of the other groups.

Since the aspirin component of this combination provides an anti-inflammatory benefit not possessed by the octadecenamide or the other capsaidin analogs, and the octadecenamide provides greater analgesia than is obtainable using aspirin alone without many of the limitative side effects of aspirin, including gastrointestinal effects, the combination clearly provides benefits not attainable using either compound alone.

EXAMPLE XV

In order to determine the preferred dosages of the capsaicinoid/non-steroidal combination in the rat, a 2:1 octadecenamide:ibuprofen analgesic composition for oral administration was made using the following ingredients:
N-vanillyl-9Z-octadeceanmide: 100 mg
Ibuprofen: 50 mg
Ethyl oleate/benzyl alcohol (98.2 vol/vol): 5 ml The two analgesics were suspended in the ethyl oleate solution with the aid of sonication, and varying dosages of the combination, as well as the individual components, were evaluated for analgesic efficacy as described in Example X.

| TREATMENT | % WRITHING RESPONSE |
|---|---|
| Ethyl oleate solution alone | 100 |
| 50 mg/kg ibuprofen | 150 |
| 100 mg/kg octadecenamide | 83 |
| 400 mg/kg octadecenamide | 21 |
| 75 mg/,kg 2:1 octadecenamide:ibuprofen combination | 40 |
| 150 mg/kg 2:1 octadecenamide: | 6 |
| 300 mg/kg 2:1 octadecenamide:ibuprofen combination | 0.5 |

All three dosage levels of the combination produced a significant analgesic effect, although the 75 mg/kg dosage produced less analgesia than the other two dosages. Preferred dosage levels will depend on the severity of the pain to be treated, the relative severity of adverse side effects, and other factors within the judgment of the physician.

Although neither 50 mg/kg ibuprofen nor 100 mg/kg octadecenamide provided significant analgesia by themselves, the 150 mg/kg combination (100 mg/kg octadecenamide + 50 mg/kg ibuprofen) demonstrated an extremely strong analgesic effect. Furthermore, only 150 mg/kg of the 2:1 combination produced a greater analgesic effect than 400 mg/kg of octadecenamide alone, and only 75 mg/kg of the 2:1 combination (subeffective amounts of both components) produced a greater analgesic effect than 100 mg/kg of octadecenamide alone. These results indicate a synergistic increase in analgesia when the two analgesics are combined.

What is claimed is:

1. An analgesic composition comprising a safe and effective amount of:
   (a) a capsaicinoid analgesic compound of the general formula:

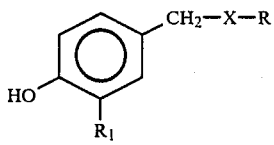

wherein $R_1$ is selected from the group consisting of OH and $OCH_3$, X is selected from the group consisting of

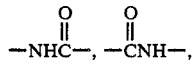

and R is a $C_{16}-C_{21}$ cis-mono-unsaturated alkenyl;
   (b) a nonsteroidal analgesic selected from the group consisting of salicylates, salicylate-like analgesic-antipyretics, and the pharmaceutically acceptable salts thereof; and
   (c) a pharmaceutically-acceptable carrier; wherein the weight ratio of (a):(b) is from about 20:1 to about 1:20.

2. A composition according to claim 1, wherein the weight ratio of (a):(b) is from about 10:1 to about 1:10.

3. A composition according to claim 2, wherein the non-steroidal is selected from the group consisting of salicylates and their pharmaceutically-acceptable salts.

4. A composition according to claim 3, wherein the non-steroidal is acetylsalicylic acid.

5. A composition according to claim 4, wherein the weight ratio of capsaicinoid to acetylsalicylic acid is from about 3:1 to about 1:3.

6. A composition according to claim 5 wherein the capsaicinoid is N-vanillyl-9-octadecenamide.

7. A composition according to claim 6, wherein the weight ratio of N-vanillyl-9-octadecenamide to acetylsalicylic acid is about 2:1.

8. A composition according to claim 3, wherein the non-steroidal is diflunisal.

9. A composition according to claim 8, wherein the weight ratio of capsaicinoid to diflunisal is from about 3:1 to about 1:3.

10. A composition according to claim 9 wherein the capsaicinoid is N-vanillyl-9-octadecenamide.

11. A composition according to claim 2, wherein the non-steroidal is selected from the group consisting of salicylate-like analgesic-antipyretics and their pharmaceutically-acceptable salts.

12. A composition according to claim 2, wherein the non-steroidal is acetaminophen.

13. A composition according to claim 12 wherein the weight ratio of capsaicinoid to acetaminophen is from about 2:1 to about 1:2.

14. A method for providing analgesia in humans and lower animals which comprises administering concurrently to a human and lower animal in need of such treatment a safe and effective amount of:
   (a) a capsaicinoid analgesic compound of the general formula:

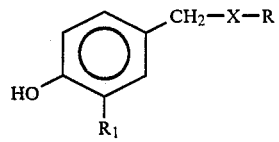

wherein $R_1$ is selected from the group consisting of OH and $OCH_3$, X is selected from the group consisting of

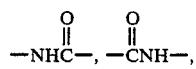

and R is a $C_{16}-C_{21}$ cis-mono-unsaturated alkenyl;
   (b) a nonsteroidal analgesic selected from the group consisting of salicylates, salicylate-like analgesic-antipyretics, and the pharmaceutically acceptable salts thereof; and wherein the weight ratio of (a):(b) is from about 20:1 to about 1:20.

15. A method according to claim 14, wherein the capsaicinoid is N-vanillyl-9-octadecenamide, the nonsteroidal is acetylsalicylic acid, and the weight ratio of N-vanillyl-9-octadecenamide to acetylsalicylic acid is from about 3:1 to about 1:3.

16. A method according to claim 14, wherein the capsaicinoid is N-vanillyl-9-octadecenamide, the nonsteroidal is difluinsal, and the weight ratio of N-vanillyl-9-octadecamide to diflunisal is from about 3:1 to about 1:3.

17. A method according to claim 14, wherein the capsaicinoid is N-vanillyl-9-octadecenamide, the nonsteroidal is acetaminophen, and the weight ratio of N-vanillyl-9-octadecenamide to acetaminaphen is from about 3:1 to about 1:3.

* * * * *